(12) United States Patent
Bungay, III et al.

(10) Patent No.: US 8,070,354 B2
(45) Date of Patent: Dec. 6, 2011

(54) SYSTEMS AND METHODS FOR MIXING BIOPROCESSING MATERIALS

(76) Inventors: Henry Robert Bungay, III, Troy, NY (US); James Steele Bungay, Rexford, NY (US); John Graul Sigsby, Glenmont, NY (US)

(*) Notice: Subject to any disclaimer, the term of this patent is extended or adjusted under 35 U.S.C. 154(b) by 975 days.

(21) Appl. No.: 12/026,054

(22) Filed: Feb. 5, 2008

(65) Prior Publication Data
US 2008/0186802 A1 Aug. 7, 2008

Related U.S. Application Data

(60) Provisional application No. 60/899,542, filed on Feb. 5, 2007.

(51) Int. Cl.
*B01F 13/00* (2006.01)
*B01F 7/00* (2006.01)
*C12M 1/00* (2006.01)
*C12M 3/00* (2006.01)

(52) U.S. Cl. ........ 366/198; 366/241; 366/142; 366/144; 366/276; 435/303.1; 435/303.3; 435/304.1; 435/307.1

(58) Field of Classification Search ........... 366/241, 366/142, 144, 198, 276; 435/303.1, 303.3, 435/304.1, 307.1
See application file for complete search history.

(56) References Cited

U.S. PATENT DOCUMENTS

| | | | |
|---|---|---|---|
| 1,607,811 A * | 11/1926 | Blum ..................... 366/110 |
| 2,673,722 A | 3/1954 | Griffen et al. |
| 3,432,149 A | 3/1969 | Stalberg et al. |
| 3,468,520 A | 9/1969 | Duryea et al. |
| 3,518,393 A | 6/1970 | Besseling et al. |
| 3,540,700 A | 11/1970 | Freedman |
| 3,819,158 A | 6/1974 | Sharpe et al. |
| 4,373,029 A | 2/1983 | Nees |
| 4,795,265 A | 1/1989 | Dahlberg et al. |
| 4,852,641 A | 8/1989 | Noble |
| 5,779,974 A | 7/1998 | Kuzyk |
| 6,142,661 A | 11/2000 | Lafond |
| 6,165,778 A * | 12/2000 | Kedar ..................... 506/33 |
| 6,267,498 B1 | 7/2001 | Lafond et al. |
| 6,273,600 B1 | 8/2001 | Sharpe |
| 6,312,151 B1 * | 11/2001 | Pendleton ............ 366/332 |
| 6,345,734 B2 | 2/2002 | Schalow et al. |
| 6,416,212 B1 * | 7/2002 | Rogers et al. ......... 366/117 |

(Continued)

OTHER PUBLICATIONS

Wave Bioreactor—FlexMixer—Part of GE Healthcare (2 pages) http://www.wavebiotech.com/products/wave_mixer/flexmixer.htm.

*Primary Examiner* — Nathan Bowers
(74) *Attorney, Agent, or Firm* — Heslin Rothenberg Farley & Mesiti P.C.; Victor A. Cardona, Esq.

(57) ABSTRACT

A system for mixing a bioprocessing fluid includes a container receiving the bioprocessing fluid and a support member supporting the container in an interior of a housing. A first channel is bounded by a first stationary arm and a second stationary arm with the first channel receiving the container. A first mixing arm and a second mixing arm are located in the interior. The first mixing arm is connected to the second mixing arm by a connecting member. The first mixing arm is located in the first channel and the second mixing arm is located in a second channel. The connecting member is movable to cause the first mixing arm to contact a first outer surface of the container to cause mixing of the bioprocessing fluid.

26 Claims, 10 Drawing Sheets

U.S. PATENT DOCUMENTS

| | | |
|---|---|---|
| 6,634,783 B2 | 10/2003 | Baron |
| 6,637,929 B2 | 10/2003 | Baron |
| 7,077,559 B2 | 7/2006 | Hlavinka et al. |
| 7,799,521 B2 * | 9/2010 | Chen .................................. 435/6 |
| 2003/0008389 A1 | 1/2003 | Carll |
| 2006/0019376 A1 | 1/2006 | Bungay III, et al. |

* cited by examiner

SYSTEMS AND METHODS FOR MIXING BIOPROCESSING MATERIALS

CROSS-REFERENCE TO RELATED APPLICATIONS

This application claims the benefit of Provisional Application Ser. No. 60/899,542 filed Feb. 5, 2007, and is related to co-pending U.S. application Ser. No. 11/186,610, filed Jul. 21, 2005, the entireties of which are incorporated by reference.

TECHNICAL FIELD

The present invention relates generally to the field of fermentation devices and more specifically to a fermentation chamber and mixing apparatus.

BACKGROUND OF THE INVENTION

The development and commercialization of many processes in the fields of medicine, chemistry, and agriculture require the use of fermentation devices or "bioreactors." As used herein, the term "fermentation" means a process for the production of a product by culturing cells or microorganisms, the process of culturing cells or microorganisms, or a process for the bioconversion of one material to another. In some bioprocesses, the organisms themselves are the desired product.

Cell culturing, for example, is often carried out in vessels that permit the contacting of cells with nutritive media and oxygen. In industrial applications, such processes are often carried out in very large vessels, often far greater than 50 liters in capacity. During research and development, however, it is generally desirable to test such processes on a much smaller scale. Historically, fermentation devices and bioreactors with volumes of 50 liters or less have suffered from various deficiencies.

Many problems with existing devices lie with the mixing mechanisms employed. Some processes use enzymes immobilized on the surfaces of particles within a liquid medium. As a result, most of the enzymatic activity is limited to the surfaces of the particles. Any method of mixing the liquid medium that causes abrasion of the particles will necessarily reduce enzymatic activity. Similar damage can be caused to cells or microorganisms within a liquid medium.

Magnetic stirrers, for example, are inapplicable to some processes, including the culturing of cells or microorganisms, because of the tendency of the magnetic stirrer, that necessarily contacts an interior surface of the vessel, to damage delicate components, such as living cells and microorganisms, that become trapped between the magnetic impeller and the vessel surface. Attempts have been made to alleviate this disadvantage through the use of super conductive materials. TC Tech Corp. (www.tc-tech.com), for example, markets a mixing device wherein a disposable impeller is levitated above the vessel's bottom, thereby eliminating the potential for entrapment of cells or microorganisms between the impeller and the vessel wall. Such devices are, however, expensive to use, due to the desirability of operating the magnets at super conducting temperatures.

U.S. Patent Application Publication No. 2003/0008389 to Carll describes a disposable cell culture vessel with a hollow sleeve in its interior, into which is placed a magnetic stirrer. In some embodiments, the sleeve is fitted with a flexible blade. Such a device also reduces or eliminates the tendency of magnetic mixers to damage delicate components. However, due in part to the fact that the mixing action of the device is provided by the simple rotation of a magnetic bar, the device is incapable of providing greater agitation or aeration of the liquid medium. Rather, the placement of a magnet within the hollow sleeve allows the gentle rotation of the impeller and the subsequent undulation of the flexible blades when an adjustable magnetic force, such as a magnetic stir plate, is applied to the vessel. This creates a gentle stirring of the cells, which keeps the cells in suspension and prevents the cells from shearing. Where more vigorous agitation or greater aeration of the liquid medium is needed, such a device is inadequate.

Other devices use blades or similar mechanisms to mix their liquid contents. U.S. Pat. No. 3,468,520 to Duryea et al., for example, describes a paddle-like mechanism residing within a bottle, which is designed to agitate a suspension of cells. Such devices, however, require the introduction of a foreign object, in the form of the mixing mechanism, into the liquid medium. This greatly increases the possibility of contamination of the medium by substances or organisms residing on the mixing mechanism. Avoidance of such contamination requires thorough cleaning and sterilization of the mixing mechanism before each use, which can greatly increase not only the burden and expense of using such devices, but also the level of technical experience required by its users.

Others have attempted to integrate the mixing mechanism into the vessel itself. U.S. Pat. No. 3,432,149 to Stalberg et al., for example, describes an apparatus for stirring a liquid having internal wings, wherein rotation of the device along its longitudinal axis exerts a dragging action on the liquid. However, such a device is capable of exerting a dragging action on only a small portion of the liquid. "The height of the liquid-dragging part of the vessel is at the most half of the intended liquid level, suitably no more than one-third thereof and preferably about one-fourth thereof." Col. 2, lines 43-46. In addition, such a device is incapable of aerating the liquid by, for example, projecting a portion of the liquid above the level of the standing liquid, thereby creating turbulence between the surface of the liquid and a gaseous layer above it.

Attempts have been made to eliminate the need for internal mixing mechanisms altogether. U.S. Pat. No. 4,373,029 to Nees, and U.S. Pat. No. 3,540,700 to Freedman et al., for example, describe devices for pivotally rotating vessels containing cells and a nutrient medium. There is a limit, however, to the degree of mixing attainable with such devices. For example, Nees notes that "acceleration magnitudes are essentially determined only by the gravity of the micro carrier in the earth's gravitational field, reduced by the viscosity of the nutrient solution." Col. 2, lines 11-14. Thus, for processes requiring a greater degree of mixing or agitation, including, for example, processes requiring greater aeration of the liquid medium, such devices are not useful.

Another method by Wave Biotech has no internal mixers and uses a flexible vessel that is pleated. The action resembles that of the bellows of an accordion. A portion of the vessel is compressed and released such that fluid in the pleats must squirt into the main bulk of the fluid to cause agitation and mixing. The pleated vessel is quite expensive to construct and cannot be scaled up to large sizes. Furthermore, the mixing is poorly related to that in commercial fermenters thus making this agitation method of questionable use when generating data for scale up.

A need exists, therefore, for a device that avoids the above described limitations. Specifically, there is a need for a fermentation chamber and mixing apparatus that (1) will not damage delicate components of the liquid medium, such as living cells and microorganisms, (2) can provide sufficient agitation of the liquid medium to ensure proper mixing and/or aeration, (3) is inexpensive to produce and use.

SUMMARY OF THE INVENTION

The present invention provides, in a first aspect, a system for mixing a bioprocessing fluid that includes flexible containers receiving the bioprocessing fluid and a means of agitation of the containers by squeezing them. The flexible containers are held in place by top portions of the containers and the containers hang in channels formed by mixing arms or bars for squeezing. Stationary arms define one channel and an adjacent channel. With two flexible containers in a channel, a movable arm between them alternately squeezes one container and releases it while squeezing and releasing the other container. In this manner, a container is bounded on one side by a fixed arm and on the other by a movable arm such that when the movable arm approaches the fixed arm the container is squeezed to create mixing within, and release of the squeezing as the movable arm departs from the fixed arm induces additional agitation as the fluid within flows back to its previous shape.

The present invention provides, in a second aspect, a system for mixing a bioprocessing fluid which includes a container receiving the bioprocessing fluid and a support member supporting the container in an interior of a housing. A first channel is bounded by a first stationary arm and a second stationary arm with the first channel receiving the container. A second channel is bounded by a third stationary arm and a fourth stationary arm with the second channel being configured to receive a second container. A first mixing arm and a second mixing arm are located in the interior. The first mixing arm is connected to the second mixing arm by a connecting member. The first mixing arm is located in the first channel and the second mixing arm is located in the second channel. The connecting member is movable to cause the first mixing arm to move toward the first stationary arm to contact a first outer surface of the container to cause mixing of the bioprocessing fluid and to cause the first mixing arm to move toward the second stationary arm to inhibit contact between the first mixing arm and the first outer surface. The second mixing arm moves toward the third stationary arm when the first mixing arm moves toward the first stationary arm and moves toward the fourth stationary arm when the first mixing arm moves toward the second stationary arm.

The present invention provides, in a third aspect, a system for mixing a bioprocessing fluid which includes a support member configured to support a container configured to receive the bioprocessing fluid in a channel in an interior of a housing. The interior is bounded by walls of the housing. A first mixing arm and a second mixing arm are located in the interior. The first mixing arm is connected to the second mixing arm by a connecting member. The channel is bounded by a first stationary arm and a second stationary arm and is configured to receive the container. The first mixing arm is located in the channel. The support member is selectively connectable to the walls of the housing to selectively adjust a height of the support member to allow containers of different heights to be received in the channel. The connecting member is movable to cause the first mixing arm to move toward the first stationary arm to contact the first outer surface of the container to cause mixing of the bioprocessing fluid and to cause the first mixing arm to move toward the second stationary arm to inhibit contact between the first mixing arm and the first outer surface when the container is received in the channel.

The present invention provides, in a fourth aspect, a system for mixing a bioprocessing fluid which includes a support member configured to support a container configured to receive the bioprocessing fluid in the channel in an interior of a housing. The interior is bounded by walls of the housing. A first mixing arm and a second mixing arm are located in the interior. The first mixing arm is connected to the second mixing arm by a connecting member. The channel is bounded by a first stationary arm and a second stationary arm and is configured to receive the container. The first mixing arm is located in the channel. The support member includes a plate having a plurality of grooves configured to be received a plurality of containers and to suspend the container in the channel. The support member includes vertical legs to support the plate. The support member is configured to be received between the walls in the interior and to be separable from the interior to support the plurality of containers outside the interior. The connecting member is to cause the first mixing arm to move toward the first stationary arm to contact a first outer surface of the container to cause mixing of the bioprocessing fluid and to cause the first mixing arm to move toward the second stationary arm to inhibit contact between the first mixing arm and the first outer surface when the container is received in the channel and the support member is received in the interior.

The present invention provides, in a fifth aspect, a method for mixing a bioprocessing fluid which includes receiving a bioprocessing fluid in a container. The container is supported via a support member in a first channel in an interior of a housing and the first channel is bounded by a first stationary arm and a second stationary arm. A second channel is bounded by a third stationary arm and a fourth stationary arm. The second channel is configured to receive a second container. A first mixing arm and a second mixing arm are located in the interior. The first mixing arm is connected to the second mixing arm by a connecting member. The first mixing arm is located in the first channel and the second mixing arm is located in the second channel. The connecting member is moved to cause the first mixing arm to move toward the first stationary arm to contact the first outer surface of the container to cause mixing of the bioprocessing fluid held in the container. The connecting member is moved to cause the first mixing arm to move toward the second stationary arm to inhibit contact between the first mixing arm and the first outer surface.

The present invention provides, in a sixth aspect, a system for mixing a bioprocessing fluid which includes a first container and a second container receiving the bioprocessing fluid. A support member is fastened to the first container and the second container in an interior of a housing. A first channel is bounded by a first stationary and a second stationary arm. The first channel receives the first container and the second container. A second channel is bounded by the second stationary arm and a third stationary arm. The second channel is configured to receive a third container and a fourth container. A first movable mixing arm is located between the first stationary arm and second station arm. The first mixing arm is movable toward the first stationary to contact the first outer surface of the first container to deform a shape of the first container to cause mixing of the bioprocessing fluid and the first mixing arm is movable in a reverse direction to move away from the first container and to contact the second container to deform the second container. A second movable mixing arm is located between the second stationary arm and the third stationary arm. The second movable mixing arm is movable toward the second stationary to contact the third outer surface of the third container to cause a mixing of the bioprocessing fluid and the second mixing arm is movable in a reverse direction to move away from the third container and to contact the fourth container to deform the fourth container.

The present invention provides, in a seventh aspect, a system for mixing a bioprocessing fluid which includes a container receiving the bioprocessing fluid. A support member supports the container in an interior of a housing. A first channel is bounded by a first stationary arm and a second stationary arm. The first channel receives the container. A second channel is bounded by a third stationary arm and a fourth stationary arm and the second channel is configured to receive a second container. A first mixing arm and a second mixing arm is located in the interior. The first mixing arm is located in the first channel and the second mixing arm is located in the second channel. The first mixing arm is movably connected to the housing to allow the first mixing arm to move toward the first stationary arm to contact the first outer surface of the container to cause mixing of the bioprocessing fluid and to allow the first mixing arm to move toward the second stationary arm to inhibit contact between the first mixing arm and the first outer surface. The second mixing arm is movably connected to the housing to allow the second mixing arm to move toward the third stationary arm and to allow the second mixing arm to move toward the fourth stationary arm.

Further, the claimed invention may use flexible bag as fermentation chambers that are inexpensive to produce and use and are capable of providing sufficient agitation of the liquid medium to ensure proper mixing and/or aeration without damaging delicate components. The invention further provides a mixing apparatus for agitating one or more such fermentation chambers. When used in processes using particle-immobilized enzymes, the invention permits adjustment of the degree of agitation of the liquid medium to ensure movement over surfaces of the particles with little or no grinding of the particles against each other.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION OF THE INVENTION

In accordance with the principles of the present invention, systems and methods for mixing bioprocessing materials are provided.

In an exemplary embodiment depicted in FIGS. 1-6, a system 5 for mixing bioprocessing materials is shown. The system may include sterile containers, such as flexible containers 14, configured to contain the bioprocessing materials (e.g., bioprocessing fluids) and configured to be supported by a supporting member or rack 15 in a base or housing 20.

Figure 1:
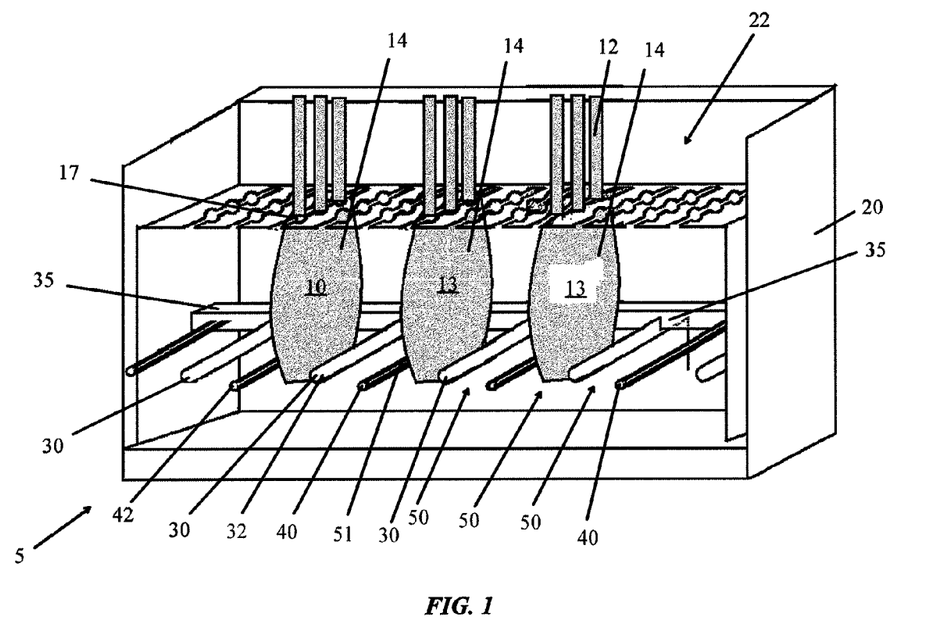
FIG. 1 is a front perspective view of a system for mixing bioprocessing fluids, wherein one or more flexible containers are suspended between elements that alternately squeeze and release the containers, in accordance with the present invention.
Figure 2:
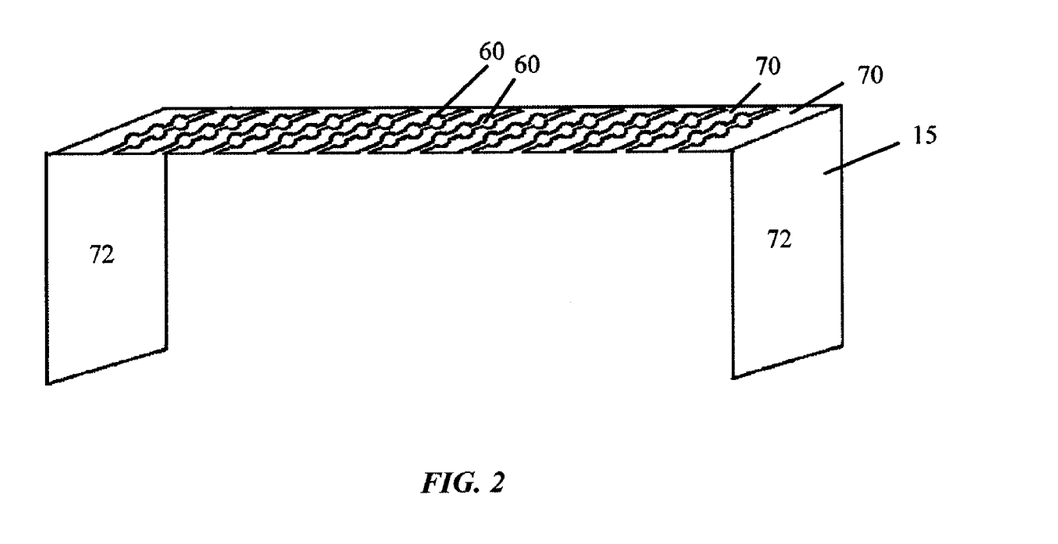
FIG. 2 is a front perspective view of a rack portion of the system shown in FIG. 1, removed from a housing thereof, in accordance with the present invention.
Figure 3:
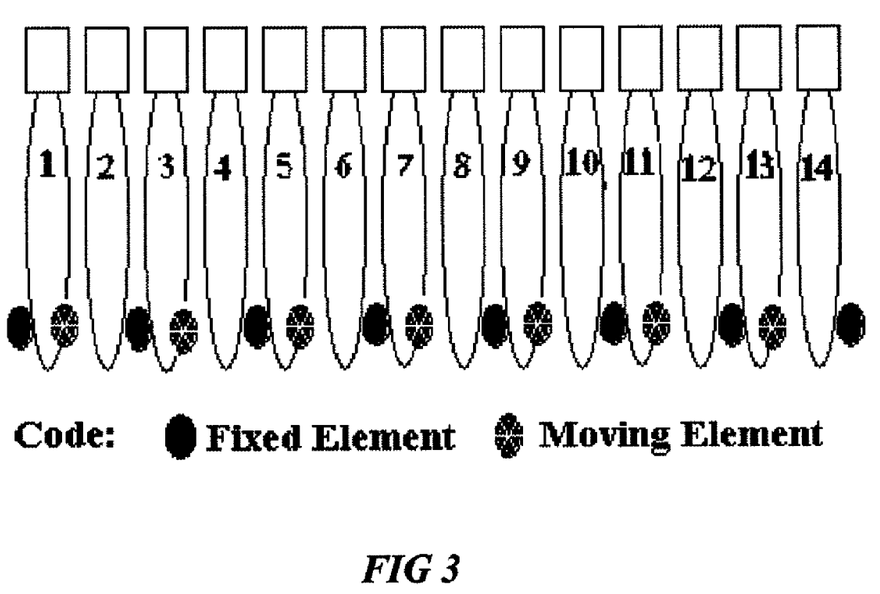
FIG. 3 is a top schematic view of the system of FIG. 1, showing fixed and movable elements thereof, in accordance with the present invention.

Housing 20 may receive rack 15 for holding flexible bags configured to hold the bioprocessing fluid. Rack 15 may also be removable from housing 20 as depicted in FIG. 2. Rack 15 includes a plate 70 having a plurality of grooves 60 configured to receive a plurality of containers (e.g., containers 14). Plate 70 may be supported by vertical legs 72 such that plate 70 may remain horizontal and support the containers (e.g., containers 14) whether the rack is inside housing 20 or outside thereof.

Container 14 may be biocompatible and may be configured to hold bioprocessing fluid such as culture medium for a fermentation as in the production of alcohol by yeast, culture medium inoculated with cells for tissue culture, biochemicals in solution to be transformed to other biochemicals by immobilized enzymes also in the fluid, growth medium for bacteria, yeast, molds, or other cells.

Further, containers (e.g., containers 14) may be connected to a rack, such as rack 15 (FIG. 1), in any number of ways. For example, each of containers 14 may have a thickened portion 17 at the intersection of conduits 12 and bag portions 13 of containers 14. Such thickened portion is the result of the additional material utilized at the connection point between the conduits and bag portions of the containers. The thickened portions may be received in grooves 60 to support the containers. For example, a frictional force provided by opposite sides of plate 70 defining each of grooves 60 may hold (e.g., support and suspend) each of containers 14 whether the rack is in housing 20 or outside thereof. Alternately, the thickened portions of the containers may be received on top of plate 70 with only bag portions 13 received in grooves 60. In the latter case, the frictional force provided by the containers in the grooves along with the support provided by the thickened portion laying on top of plates 70 may suspend and support the containers. Also, in another embodiment depicted in FIG. 5, a container 210 may have grommets 220 to receive pins (not shown) of another rack (not shown) to connect container 210 to the rack.

Also, a plurality of mixing rods or arms 30 may be attached to a connecting bar or member 35 such that both the mixing arms and connecting member move laterally, i.e., longitudinally relative to rack 15 and base 20. Each of mixing arms 30 may be located in one of channels 50 between two of stationary arms 40 bounding and defining such channels. The mixing arms that may thus move between opposite stationary arms. Also, the mixing arms may be movably and/or releasably connectable to connecting member 35 such that the distance between each mixing arms and the opposing stationary arms may be selectively adjusted. For example, a mixing arm 32 may be connected to connecting member 35 at a location relatively far away from a stationary arm 42 such that relative movement between mixing arm 32 and stationary arm 42 is maximized or mixing arm 32 may be connected to connecting member 35 at a location relatively close to stationary arm 42 such that relative movement between mixing arm 32 and stationary arm 42 is minimized. An amount of contact between mixing arm 32 and a container 10 of containers 14 may thus be controlled by the attachment point of a mixing arm (e.g., mixing arm 32) relative to the connecting arm (e.g., connecting arm 35). Further, the intermittent contact of mixing arms 30 with containers 14 by back and forth motion of the mixing arms between the stationary arms causes mixing of the materials held therein. The contact of containers 14 by the mixing arms provides a simple, cost-effective method for agitation of fermentation and bioprocessing fluids. Such contact may squeeze and release the containers to provide movement to liquid (e.g., bioprocessing liquid) in the containers. In particular, squeezing of the containers distorts a shape of the flexible containers to cause motion to the liquid held therein and a release of the container also causes a distortion of the shape of the container to provide further movement to the liquid.

Containers 14 may be placed into grooves 60 of rack 20 when rack 20 is located in an interior 22 of housing 20 or the containers may be placed into the grooves prior to the rack being placed into interior 22 such that rack 20 is inserted into the interior with the containers already attached thereto. In this manner, a second run or processing (e.g., mixing) operation may be prepared while a first run is in progress. The first run may be terminated simply by removing a rack holding the containers therefor, and the second run may start soon after by substituting a different rack with containers attached thereto. Further, one or more containers 14 may be removed and replaced with other containers without terminating an entire run. Also, as indicated above, the rack may be removed from the housing, which may allow the containers to be filled outside the housing and/or otherwise have measurements taken thereof outside the housing. In a further unillustrated example, a housing (e.g., housing 20) may include a tray for receiving spills or condensation from containers held in housing 20. Such a tray may be located on a bottom surface of such a housing.

Figure 4:
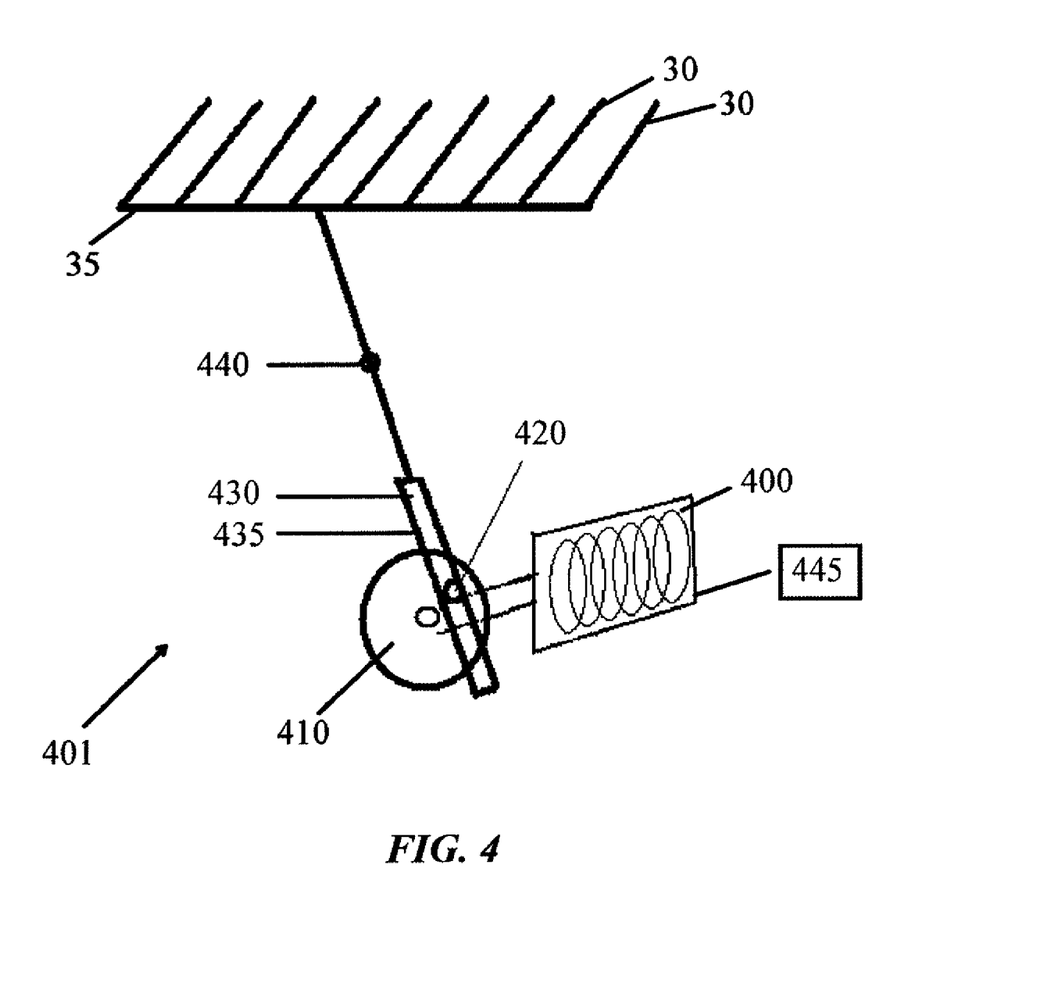
FIG. 4 is a simplified view of a motor and mechanism for moving a connecting member and mixing arms of the system of FIG. 1, in accordance with the present invention.
Figure 5:
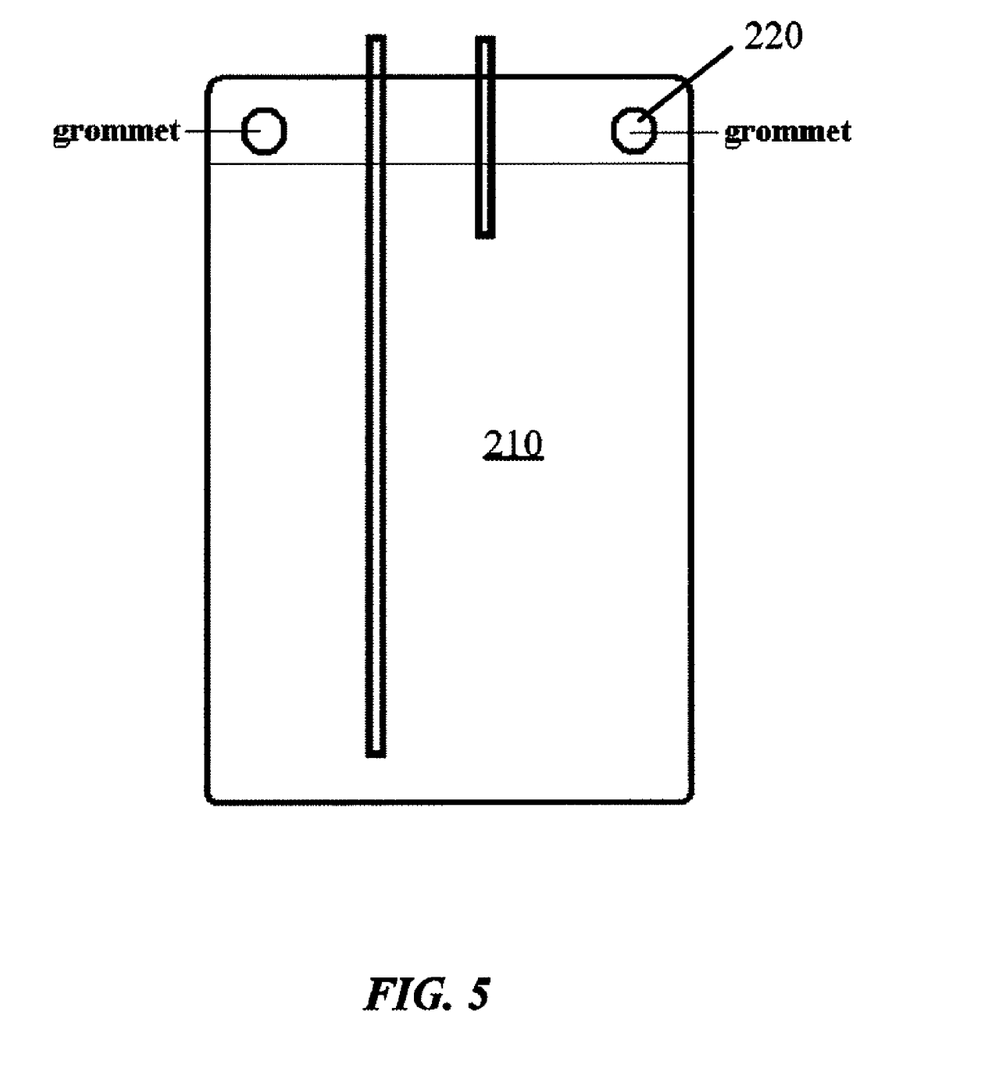
FIG. 5 is a side view depicting an embodiment of a container attachable to pins of a support member, in accordance with the present invention.

As depicted in FIG. 4, the mixing arms and connecting member may be rotated via a driving mechanism 401 which includes a motor 400 and a wheel 410 or any other means of providing such motion. For example, motor 400 may turn wheel 410 which has a pin 420 attached thereto. The pin fits into a slot 430 of a bar 435 on a pivot 440 which may be stationary and attached to housing 20, for example. As the wheel turns driven by the motor, the pin moves back and forth to translate its motion to the slotted bar that in turn, through the pivoting action, moves (e.g., via reciprocating back-and-forth motion) the connecting member and mixing arms. The motor may be controlled by a computing unit 445 which may regulate a speed and timing of motion of the connecting member and mixing arms by controlling the motor. Further, as will be understood by one skilled in the art, the mixing arms and connecting member may be driven by any number of drivers including eccentric mechanisms, solenoids, electric motors, or linear actuators.

Also, the mixing arms may include one or more sensors 51 (e.g., temperature sensor or photo sensor, FIG. 1) which may be coupled to a computing unit (e.g., computing unit 445, FIG. 4) controlling the movement of the connecting member and mixing arms to optimize mixing of bioprocessing fluid held in the container. For example, the information received (e.g., temperature, turbidity) from such a sensor may provide feedback which may allow the motor to be more efficiently controlled to provide mixing to bioprocessing fluid held in a container in the housing, such as container 10 received in one of channels 50 subject to mixing by mixing arm 32 as described above in depicted in FIG. 1. For example, the sensors may be thermometers, or optical sensors coupled to light sources for detecting turbidity or color intensity of the contents of the container(s). In another example, one or more heating elements (e.g., resistive heating elements) may be located on one or more mixing arms (e.g., mixing arm 32) or stationary arms (e.g., stationary arm 42) to heat bioprocessing fluid held in a container abutting such mixing arm or stationary arm. Further, such heating elements may be coupled to a controller to allow a temperature of the bioprocessing fluids held in the container(s) to be regulated via such controller, which may also be coupled to the sensors described above to better regulate the temperature and other characteristics of bioprocessing fluids held in the containers.

Figure 6:
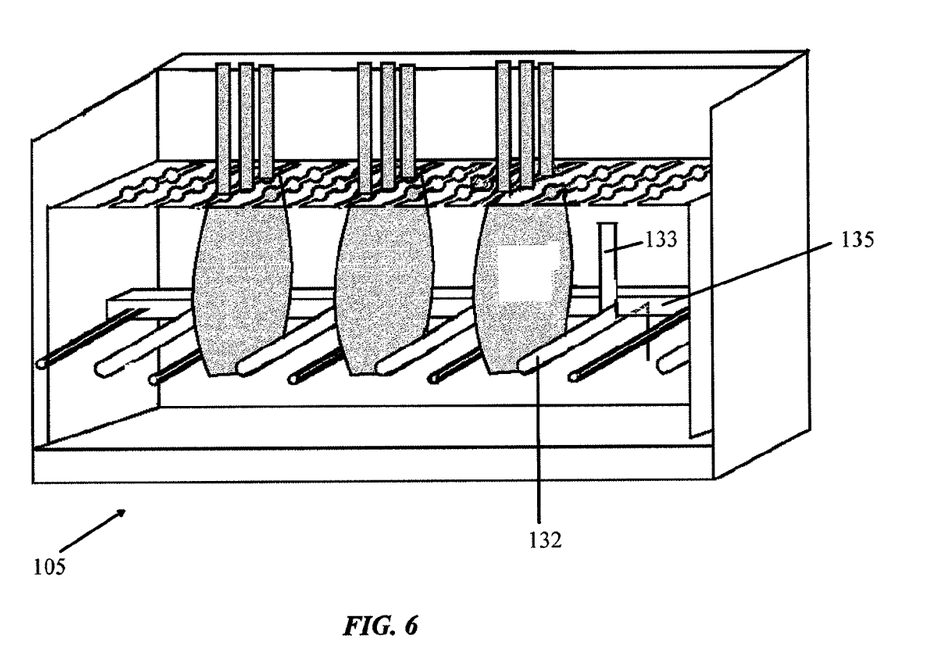
FIG. 6 is a front perspective view of another embodiment of a system for mixing bioprocessing fluids which includes a vertically adjustable mixing arm, in accordance with the present invention.

Also, in an example depicted in FIG. 6, a system 105 for mixing bioprocessing materials may include mixing arms 40 which are vertically adjustable. For example, a movable connection of a mixing arm 132 to a vertical member 133 attached to a connecting member 135 may allow mixing arm 132 to be selectively vertically adjustable. The vertical adjustability of the mixing arm may allow contact of the mixing arms (e.g., mixing arm 132) with the containers at various heights relative to the containers as desired. The remaining components of system 105 depicted in FIG. 6 are identical to those in FIG. 1. Also, a rack and/or housing, such as rack 15 and/or housing 20, may be of differing heights to allow different sized containers to be used.

Figure 7:
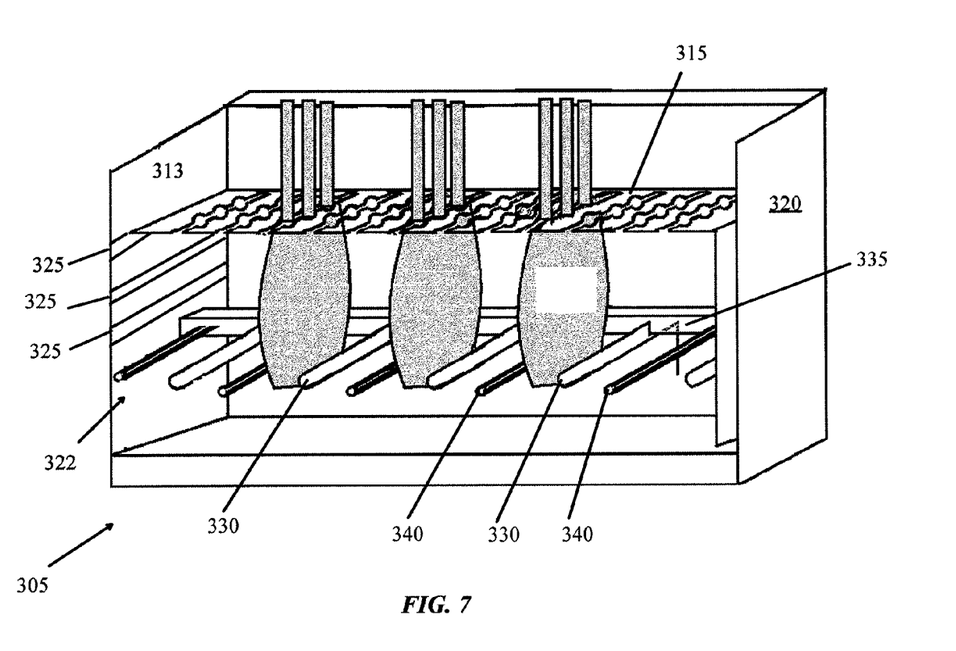
FIG. 7 is a front perspective view of a further embodiment of a system for mixing bioprocessing fluids which includes a support member which is adjustable in various slots of a housing thereof, in accordance with the present invention.

In another example, depicted in FIG. 7, a system 305 for mixing bioprocessing materials may include a housing 320, connecting member 335, mixing arms 330 and stationary arms 340. System 305 is similar to system 5 except that a rack 315 is connected to interior walls 323 of housing 320. In particular, rack 315 may be attached to the walls by being received in slots 325 at one of various heights to allow the selective height adjustment of the rack. Rack 315 could also be attached via bolts (not shown) or by resting on shelves or protrusions (not shown) in an interior (e.g., interior 322) of a housing (e.g., housing 320). Such height adjustment of rack 315 may allow the use of various sized containers (e.g., containers 14) within system 305. Rack 315 may support and may be attached to such containers as described above for rack 15. The vertical location of the mixing arms for good mixing and agitation of the contents may be different for bags of different lengths. The vertical location of the mixing arms relative to the containers may be adjusted by varying the height of the rack, such as via multiple slots, grooves or shelves in walls 323 for receiving the rack.

Figure 8:
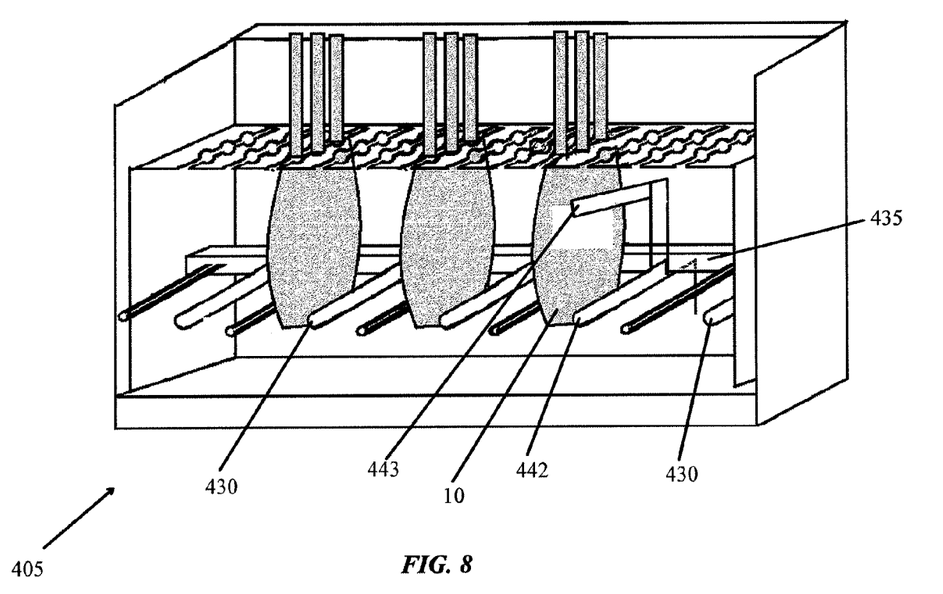
FIG. 8 is a front perspective view of a further embodiment of a system for mixing bioprocessing fluids which includes multiple vertically aligned mixing arms for contacting a container holding bioprocessing fluids, in accordance with the present invention.
Figure 9:
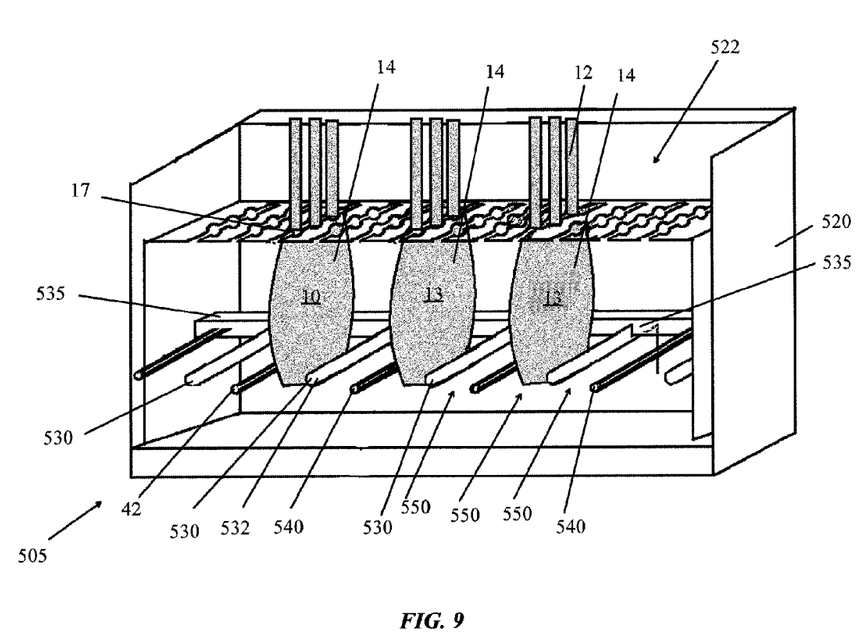
FIG. 9 is a front perspective view of yet a further embodiment of a system for mixing bioprocessing fluids which includes mixing arms pivotally connected to a housing and movable between stationary arms to contact flexible containers holding bioprocessing fluids, in accordance with the present invention.

Also, in another example depicted in FIG. 8, a system 405 for mixing bioprocessing materials may include a connecting member 435 connected to multiple mixing arms 430 such that the arms may be located in different vertical positions. For example, a first mixing arm 443 and a second mixing arm 442 may contact a container 10 at different vertical positions relative to container 10 and the arms may be substantially vertically aligned with each other. Each of the vertical arms may also be vertically adjustable and/or longitudinally adjustable relative to connecting arm 435. The remaining features of system 405 depicted in FIG. 8 are identical to that in FIG. 1. Alternatively, a system utilizing multiple vertical and/or horizontal mixing arms which are vertically and/or horizontally adjustable may also be utilized with a support member such as that depicted in FIG. 7.

Further, the containers (e.g., containers 14) described above may be received in a bath of water or other fluid for controlling a temperature of the bioprocessing materials held therein. The adjustability of the mixing arms (e.g., mixing arms 130) and/or the rack (e.g., rack 15 or rack 315) may allow the containers to be supported such that the mixing arms contact a container (e.g., containers 14) above such a water or fluid bath. Alternatively, the mixing arms could have a shape to allow them to contact the container within such a water or fluid bath.

Figures 10, 11, 12:
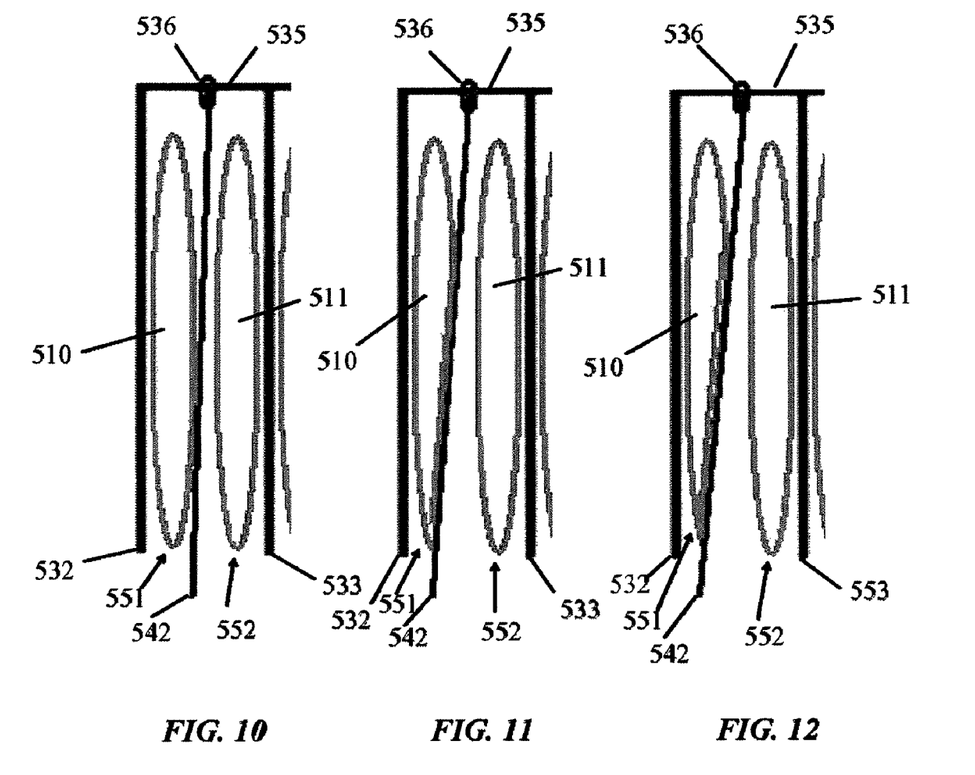
FIG. 10 is a simplified line drawing of a top view of the system of FIG. 9 showing a mixing arm moving toward a stationary arm.
FIG. 11 is a simplified line drawing of a top view of the system of FIG. 10 showing the mixing arm of FIG. 10 moving further toward the stationary arm.
FIG. 12 is a simplified line drawing of a top view of the system of FIG. 11 showing the mixing arm moving yet further toward the stationary arm.

In another example depicted in FIGS. 9-12, a system 505 for mixing bioprocessing fluid materials (e.g., fluids) may include a connecting member 535 connected to multiple mixing arms 530. The mixing arms are pivotally connected to the connecting arm such that they may move toward and away from stationary arms 540 within channels 550. As depicted in FIG. 10 in simplified form, a first channel 551 may be separated from a second channel 552 by a pivotally mounted mixing arm 542 connected to stationary connecting member 535 at a connection point 536. As further depicted in FIGS. 10-12, mixing arm 542 may move toward a first stationary arm 532 to contact a container 510 to deform a shape of the container and cause mixing of the bioprocessing materials held therein. Further, mixing arm 542 may move toward a second stationary arm 533 to contact second container 511 to deform a container and cause mixing of the bioprocessing fluids held therein. The pivotal connection of mixing arm 542 to connecting arm 535 allows the mixing of the bioprocessing fluids held in the containers without movement of connecting member 535. Alternatively, such pivoting arms could be connected to a housing 520 in another manner besides connection to a single connecting arm such as connecting arm 535. As described above relative to the other examples, the mixing arms could also be vertically adjustable. Further, the mixing arms (e.g., mixing arm 542) may be driven by a motor to cause the movement of the mixing arms between the adjacent stationary arms (e.g., stationary arms 532 and 533).

In an unillustrated example, containers holding bioprocessing fluids may be supported by a rack in a base, such as rack 15 in base 20 and mixing of bioprocessing fluids held in the containers may be caused by an inflatable bag or other inflatable device which may be repeatedly inflated to cause pressure on the containers to intermittently deform the containers to cause motion of the bioprocessing fluids and mixing thereof. For example, such an inflatable device may be located between two containers such that they both may be deformed by the inflatable device or the inflatable device may be located between a stationary object, such as a stationary arm, and such a container receiving bioprocessing fluids to cause the deformation of such a container and allow mixing thereof.

The containers (e.g., containers 14) described above and depicted in the figures (e.g., FIG. 1) have three ports, but as will be understood once skilled in the art containers with fewer or with more ports may also be utilized. Further, any number of containers may be utilized based only on the number of channels, mixing arms, and stationary arms providing in a particular system for mixing bioprocessing materials. Also, the containers (e.g., containers 14) may also have sensors in the ports thereof to monitor various aspects (e.g., temperature or turbidity) of bioprocessing material held in the containers. Further, the contents of the containers may also be monitored for pH, nutrient concentrations, and/or product concentrations via such sensors received in such ports. Such sensors may be coupled to a computing unit, such as computing unit 445 (FIG. 4). Also, the containers may be applicable to a wide variety of processes, including the culturing of living cells and microorganisms. Further, the containers could be hanging bag(s) that may be associated with electrodes, tubing, or other devices that enter the bag. Such containers may be totally transparent or have regions of transparency, and light may be used to monitor changes in the turbidity or color of the contents. As described, the light source and light detector can be associated with the mixing arms.

Further, the mixing arms (e.g., mixing arms 30), stationary arms (e.g., stationary arms 40), connecting member (e.g., connecting member 35), rack (e.g., rack 15, rack 315) and housing (e.g., housing 20, housing 320) may be formed of metal, ceramic, plastic, glass, or various composites. The containers (e.g., containers 14) may be made of any flexible material configured to hold the bioprocessing materials such as plastic or rubber. For example, the containers may be formed of high-density polyethylene or polypropylene that can withstand sterilization in a steam autoclave.

The containers may be as small as 50 ml and as large as 4 liters for bags supported only at top portions thereof, for example. A limitation on the size of containers held by top portions thereof (e.g., in grooves 60) is the breaking strength of plastic forming such a container. An upper limit of such container can extend to tens of liters if the bag rests in a supporting basket instead of being supported by a top portion thereof, for example. As described above, the rack may be vertically adjusted relative to a size of a container to be mixed. Also, the mixing arms may be adjusted along the connecting member to regulate a length of reciprocation of the arm and also to accommodate different sized containers.

While this invention has been described in conjunction with the specific embodiments outlined above, it is evident that many alternatives, modifications, and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:
1. A system for mixing a bioprocessing fluid comprising:
a container receiving the bioprocessing fluid;
a support member supporting said container in an interior of a housing;
a first channel bounded by a first stationary arm and a second stationary arm, said first channel receiving said container;

a second channel bounded by a third stationary arm and a fourth stationary arm and, said second channel configured to receive a second container;
a first mixing arm and a second mixing arm located in said interior, said first mixing arm connected to said second mixing arm by a connecting member, said first mixing arm located in said first channel and said second mixing arm located in said second channel;
said connecting member movable to cause said first mixing arm to move toward said first stationary arm to contact a first outer surface of said container to cause mixing of the bioprocessing fluid and to cause said first mixing arm to move toward said second stationary arm to inhibit contact between said first mixing arm and said first outer surface; and
said second mixing arm moving toward said third stationary arm when said first mixing arm moves toward said first stationary arm and said second mixing arm moving toward said fourth stationary arm when said first mixing arm moves toward said second stationary arm.

2. The system of claim 1 wherein said first mixing arm is movably connected to said connecting member to allow a selective adjustment of a location of said first mixing arm in said first channel along said connecting member.

3. The system of claim 1 wherein said first mixing arm is movably connected to said to connecting member to allow a selective adjustment of a location of said first mixing arm in said channel, said adjustment being in a vertical direction substantially perpendicular relative to a longitudinal direction of said connecting member.

4. The system of claim 1 further comprising a driving mechanism coupled to said connecting member to reciprocate said connecting member.

5. The system of claim 1 wherein said first mixing arm comprises a sensor for determining at least one of a temperature and a turbidity of the bioprocessing fluid.

6. The system of claim 1 wherein said connecting member extends longitudinally substantially perpendicularly relative to longitudinal dimensions of said first arm and said second arm.

7. The system of claim 1 wherein said support member comprises a plate having a plurality of grooves configured to receive a plurality of containers, said container received in a groove of said plurality of grooves and suspended in said channel.

8. The system of claim 7 wherein said support member comprises vertical legs supporting said plate and said support member separable from said housing to allow said support member to support the plurality of containers outside said interior.

9. The system of claim 1 wherein said first mixing arm comprises a heating element for heating the bioprocessing fluid received in the container.

10. The system of claim 1 wherein said second stationary arm and said third stationary arm comprise a same stationary arm.

11. A system for mixing a bioprocessing fluid comprising:
a support member configured to support a plurality of containers configured to receive the bioprocessing fluid in an interior of a housing;
a first mixing arm and a second mixing arm located in said interior, said first mixing arm coupled to said second mixing arm;
a first channel bounded by a first stationary arm and a second stationary arm and configured to receive a first container, said first mixing arm located in said channel; and
a second channel bounded by a third stationary arm and a fourth stationary arm and configured to receive a second container, said second mixing arm located in said second channel;
said first mixing arm movable toward said first stationary arm simultaneously with said second mixing arm moving toward said third stationary arm to cause mixing of the bioprocessing fluid and said second mixing arm simultaneously movable toward said fourth stationary arm when said first mixing arm moves toward said second stationary arm to inhibit contact between said first mixing arm and said second mixing arm and the plurality of containers.

12. The system of claim 11 wherein said second stationary arm and said third stationary arm comprise a same stationary arm.

13. A system for mixing a bioprocessing fluid comprising:
a support member configured to support a plurality of containers configured to receive the bioprocessing fluid in an interior of a housing;
a first mixing arm and a second mixing arm located in said interior, said first mixing arm coupled to said second mixing arm;
a first channel bounded by a first stationary arm and a second stationary arm and receiving a first container of said plurality of containers, said first mixing arm located in said first channel; and
a second channel bounded by a third stationary arm and a fourth stationary arm and receiving a second container of said plurality of containers, said second mixing arm located in said second channel;
said first mixing arm movable toward said first stationary arm to contact a first outer surface of the first container simultaneously with said second mixing arm moving toward said third stationary arm to contact a second outer surface of said second container to cause mixing of the bioprocessing fluid and said second mixing arm simultaneously movable toward said fourth stationary arm when said first mixing arm moves toward said second stationary arm to inhibit contact between said first mixing arm and said first outer surface and said second mixing arm and said second outer surface.

14. The system of claim 13 wherein said second stationary arm and said third stationary arm comprise a same stationary arm.

15. A method for mixing a bioprocessing fluid, the method comprising:
receiving bioprocessing fluid in a container;
supporting the container via a support member in a first channel in an interior of a housing, the first channel bounded by a first stationary arm and a second stationary arm;
bounding a second channel by a third stationary arm and a fourth stationary atm, the second channel configured to receive a second container;
locating a first mixing arm and a second mixing arm in the interior, the first mixing arm connected to the second mixing arm by a connecting member, the first mixing arm located in the first channel and the second mixing arm located in the second channel;
moving the connecting member to cause the first mixing arm to move toward the first stationary arm to contact a first outer surface of the container to cause mixing of the bioprocessing fluid held in the container;

moving the connecting member to cause the first mixing arm to move towards the second stationary arm to inhibit contact between the first mixing arm and the first outer surface;

moving the second mixing arm toward the third stationary arm when the first mixing anon moves toward the first stationary arm; and moving the second mixing arm toward the first stationary arm when the first mixing moves toward the second stationary arm.

16. The method of claim 15 further comprising receiving the container in a groove of the support member to support the container in the channel.

17. The method of claim 15 further comprising removing the support member from the interior of the housing and suspending the container by the support member on a plurality of legs outside said interior.

18. The method of claim 15 further comprising selectively adjusting a height of the support member to allow a second container to be received in the channel.

19. The method of claim 15 further comprising selectively adjusting a height of the first mixing arm relative to the connecting member.

20. The method of claim 15 further comprising selectively adjusting a distance between the first mixing arm and the first stationary arm.

21. The method of claim 15 wherein the second stationary arm and the third stationary arm comprise a same stationary arm.

22. A system for mixing a bioprocessing fluid comprising:
a first container and a second container receiving the bioprocessing fluid;
a support member to fasten said first container and said second container in an interior of a housing;
a first channel bounded by a first stationary arm and a second stationary arm, said first channel receiving said first container and said second container;
a second channel bounded by said second stationary arm and a third stationary aria, said second channel configured to receive a third container and a fourth container;
a first movable mixing arm between said first stationary arm and said second stationary arm;
said first mixing arm movable toward said first stationary arm to contact a first outer surface of said first container to deform a shape of said first container to cause mixing of the bioprocessing fluid and said first mixing arm movable in a reverse direction to move away from said lust container and to contact said second container to deform said second container;
a second movable mixing arm between said second stationary arm and said third stationary arm; and
said second movable mixing arm movable toward said second stationary arm to contact a third outer surface of said third container to cause a mixing of the bioprocessing fluid and said second mixing arm movable in a reverse direction to move away from said third container and to contact said fourth container to deform said fourth container.

23. A system for mixing a bioprocessing fluid comprising:
a container receiving the bioprocessing fluid;
a support member supporting said container in an interior of a housing;
a first channel bounded by a first stationary arm and a second stationary arm, said first channel receiving said container;
a second channel bounded by a third stationary arm and a fourth stationary arm and said second channel configured to receive a second container;
a first mixing arm and a second mixing arm located in said interior, said first mixing arm located in said first channel and said second mixing arm located in said second channel;
said first mixing arm movably connected to said housing to allow said first mixing arm to move toward said first stationary arm to contact a first outer surface of said container to cause mixing of the bioprocessing fluid and to allow said first mixing arm to move toward said second stationary arm to inhibit contact between said first mixing arm and said first outer surface; and
said second mixing arm movably connected to said housing to allow said second mixing atm to move toward said third stationary arm and to allow said second mixing arm to move toward said fourth stationary arm.

24. The system of claim 23 further comprising at least one driver connected to said first mixing arm and configured to cause said first mixing arm to move toward said first stationary arm and to move away from said first stationary arm toward said second stationary arm.

25. The system of claim 23 wherein said second stationary arm and said third stationary arm comprise a same stationary arm.

26. The system of claim 23 wherein said first mixing arm is pivotally connected to said housing.

* * * * *